United States Patent
Li et al.

(10) Patent No.: US 11,692,952 B1
(45) Date of Patent: Jul. 4, 2023

(54) HYDRO-MECHANICAL COUPLING EXPERIMENTAL DEVICE WITH CT REAL-TIME SCANNING AND USE METHOD THEREOF

(71) Applicant: Anhui University of Science and Technology, Huainan (CN)

(72) Inventors: Shaobo Li, Huainan (CN); Lei Wang, Huainan (CN); Qihan Ren, Huainan (CN); Xingang Niu, Huainan (CN); Chuanqi Zhu, Huainan (CN); Lipeng Chen, Huainan (CN); Yu Zhang, Huainan (CN); Ancheng Wang, Huainan (CN)

(73) Assignee: Anhui University of Science and Technology, Huainan (CN)

( * ) Notice: Subject to any disclaimer, the term of this patent is extended or adjusted under 35 U.S.C. 154(b) by 0 days.

(21) Appl. No.: 18/179,157

(22) Filed: Mar. 6, 2023

(30) Foreign Application Priority Data

Apr. 6, 2022 (CN) .......................... 202210359442.X (51) Int. Cl.
  G01N 23/00 (2006.01)
  G01N 23/046 (2018.01)
  G01N 1/28 (2006.01)
(52) U.S. Cl.
  CPC ............. *G01N 23/046* (2013.01); *G01N 1/28* (2013.01)
(58) Field of Classification Search
  CPC .................................................. G01N 23/046
  See application file for complete search history.

(56) References Cited

U.S. PATENT DOCUMENTS

2015/0168282 A1 6/2015 He et al.
2016/0216218 A1* 7/2016 Grader ............... A61K 38/1816

FOREIGN PATENT DOCUMENTS

| CN | 105181471 A | 12/2015 |
| CN | 106872670 A | 6/2017 |
| CN | 108088860 A | 5/2018 |
| CN | 109580365 A | 4/2019 |

(Continued)

OTHER PUBLICATIONS

First Office Action issued in counterpart Chinese Patent Application No. 202210359442.X, dated Aug. 24, 2022.

(Continued)

*Primary Examiner* — Dani Fox
(74) *Attorney, Agent, or Firm* — Westbridge IP LLC (57) ABSTRACT

Disclosed are a hydro-mechanical coupling experimental device with CT real-time scanning and a use method thereof. The hydro-mechanical coupling experimental device with the CT real-time scanning includes a CT scanning room and further includes a support frame, a hydro-mechanical coupling mechanism and a jack that are arranged in the CT scanning room. The support frame includes a base, a top plate, a plurality of columns for arranging the top plate and the base at intervals, and a movable plate that is arranged between the top plate and the base and can slide on the plurality of columns. The hydro-mechanical coupling mechanism includes an experimental box, a pressure box arranged inside the experimental box and a compression leg slidingly worn on a top of the experimental box; and the experimental box is arranged on the movable plate, and the jack is arranged on the base.

8 Claims, 6 Drawing Sheets

(56) References Cited

FOREIGN PATENT DOCUMENTS

| CN | 110542614 A | 12/2019 |
|---|---|---|
| CN | 111811943 A | 10/2020 |
| CN | 112858024 A | 5/2021 |
| CN | 113324837 A | 8/2021 |
| CN | 214472285 U | 10/2021 |
| CN | 113758807 A | 12/2021 |

OTHER PUBLICATIONS

International Search Report issued in counterpart PCT Application No. PCT/CN2022/087426, dated Dec. 19, 2022.

Jia, The Experiment Study on the Creep-Seepage Coupling in Process of Coal Failure, Master Thesis submitted to Liaoning Technical University, dated Mar. 15, 2017.

Qi et al., Experimental Study on Effect of Water Immersion Coupling on Coal Strength, Coal Technology, vol. 41, No. 01, pp. 4-7, dated Jan. 10, 2022.

Wang, Experimental Study on Acoustic Emission Monitoring and Fracture Instability Characteristic during Hydraulic Fracturing in Coal, Master Thesis submitted to Anhui University of Science and Technology, dated Aug. 15, 2016.

Zhou, The Research on the Characteristics of Evolution of Borehole Strain Behavior Induced by Hydraulic Fracturing, Master Thesis submitted to Anhui University of Science and Technology, dated Jul. 15, 2015.

\* cited by examiner

HYDRO-MECHANICAL COUPLING EXPERIMENTAL DEVICE WITH CT REAL-TIME SCANNING AND USE METHOD THEREOF

CROSS-REFERENCE TO RELATED APPLICATIONS

The application claims priority to Chinese Patent Application 202210359442.X, filed on Apr. 6, 2022, which is incorporated herein by reference in its entirety.

TECHNICAL FIELD

The present disclosure relates to the technical field of rock mechanical experiments, in particular to a hydro-mechanical coupling experimental device with computed tomography (CT) real-time scanning and a use method thereof.

BACKGROUND

At present, our country has entered the deep mining stage, groundwater is of great influence on the stability and deformation of coal and rock mass in deep mines, and mine disasters caused by the groundwater are common. According to the relevant report, over the past few decades, at least 300 big and small mines in our country occurred water inrush accidents, resulting in significant casualties and serious economic losses. Underground water of a coal mine can change physical and mechanical properties of the coal and rock mass, and is of great influence on leaving a coal pillar and safe mining under confined water, therefore it is urgent to study the influence of water on the mechanical properties of the coal and rock mass and to effectively prevent and control the influence.

Damage evolution rules of the coal and rock mass under a water immersion environment are researched for hydro-mechanical coupling engineering problems, such as underground flooding of the coal mine and water immersion of the coal pillar. However, most of the existing researches are to measure the mechanical properties of the coal and rock mass when the coal and rock mass is separated from liquid and a hydraulic pressure environment after being immersed, the mechanical properties of the immersed coal and rock mass cannot be really restored, and due to limitations of experimental conditions, mesomechanics destructive characteristics inside the coal and rock mass cannot be observed in real time, and therefore, it is now necessary to develop a hydro-mechanical coupling experimental device with a CT real-time scanning system.

SUMMARY

The technical problem to be solved by the present disclosure is to provide a hydro-mechanical coupling experimental device with a CT real-time scanning system and a use method thereof, which can not only restore mechanical properties of immersed coal and rock mass, but also observe mesomechanics destructive characteristics inside the coal and rock mass in real time.

In order to solve the above technical problem, the present disclosure adopts the following technical solution: a hydro-mechanical coupling experimental device with CT real-time scanning, including a CT scanning room, further including a support frame, a hydro-mechanical coupling mechanism and a jack that are arranged in the CT scanning room; and the support frame includes a base, a top plate, a plurality of columns for arranging the top plate and the base at intervals, and a movable plate that is arranged between the top plate and the base and can slide on the plurality of columns. The hydro-mechanical coupling mechanism includes an experimental box, a pressure box arranged inside the experimental box and a compression leg slidingly worn on a top of the experimental box; and the experimental box is arranged on the movable plate, and the jack is arranged on the base;

the the hydro-mechanical coupling mechanism further includes a regulating assembly, and the regulating assembly includes an operation block, a first threaded rod and two first limiting members; and one end, located in the experimental box, of the compression leg is provided with a first installation groove, screws at two sides of the first threaded rod are symmetrically arranged, two ends of the first threaded rod are rotationally arranged on groove walls of two sides of the first installation groove in respective, and one end of the first threaded rod passes through the first installation groove and the compression leg to be connected to the operation block; and the two first limiting members are in threaded connection with the two sides of the first threaded rod in respective, and the two first limiting members are slidingly connected to the groove wall of the first installation groove in respective.

Further, the experimental box includes a housing with an operation port, a water inlet and a water outlet, a tempered transparent glass plate for sealing the housing and two valves for controlling the water inlet and the water outlet to be opened and closed.

Further, the hydro-mechanical coupling mechanism further includes a stress-strain data acquisition instrument; a trunking, through which a data wire of the pressure box can pass through, is also arranged on the housing; and a waterproof gasket is arranged on a groove wall of the trunking, and the stress-strain data acquisition instrument is connected to the pressure box through the data wire.

Further, the regulating assembly further includes a second threaded rod, a third threaded rod and two second limiting members that are symmetrically arranged;

one end, located in the experimental box, of the compression leg is also provided with a second installation groove communicating with the first installation groove, one end of the second threaded rod is rotationally connected to a groove wall of one side of the second installation groove while the other end is connected to a first gear, and one end of the third threaded rod is rotationally connected to a groove wall of the other side of the second installation groove while the other end is connected to a second gear; and the two second limiting members are in threaded connection with the second threaded rod and the third threaded rod in respective, and the two second limiting members are slidingly connected to the groove wall of the second installation groove in respective;

a third gear is arranged in a middle of the first threaded rod, a fourth gear is rotationally arranged on the groove wall of the first installation groove, the fourth gear meshes with the third gear, and the first gear and the second gear mesh with two sides of the fourth gear in respective.

Further, the first limiting members and the second limiting members are of the same structure and all include a sliding block, a connecting strip connected to the sliding block, and a baffle vertically connected to the connecting strip.

Further, a spring is wound on each column, and the spring is located between the movable plate and the top plate; and two ends of the spring are respectively connected to the movable plate and the top plate.

Further, the support frame further includes two fixed assemblies that are symmetrically arranged, and each fixed assembly includes a fixed plate, a fourth threaded rod and a fixed block; and the fixed plate is arranged on the base, the fourth threaded rod is in threaded connection with the fixed plate, and the fixed block is rotationally connected to one end of the fourth threaded rod and slidingly connected to the base.

A use method for a hydro-mechanical coupling experimental device with CT real-time scanning, which is applied in a hydro-mechanical coupling experimental device with the CT real-time scanning, and the steps are as follows:

S1: preparing a standard coal and rock sample;

S2: opening a tempered transparent glass plate, placing the coal and rock sample on a pressure box, and regulating a regulating assembly so that the coal and rock sample is adjusted and located at a central position of the pressure box and a top of the coal and rock sample is partially located between first limiting members and second limiting members;

S3: fixing the tempered transparent glass plate, sealing a housing, opening valves of a water inlet and a water outlet, accessing purified water with pressure into the sealed housing through the water inlet until a whole experimental box is full of the purified water, and closing the valves of the water inlet and the water outlet;

S4: standing the coal and rock sample in the purified water for a period of time, where the time range is 24-48 hours; and S5: after standing, opening a jack to push a movable plate, opening CT scanning and receiving equipment of a CT scanning room and opening a stress-strain data acquisition instrument for data acquisition, and recording a strength, a deformation, a surface morphology and evolution rules of mesomechanics destructive characteristics of the sample in real time under in-situ loading conditions of hydro-mechanical coupling.

The present disclosure has the following beneficial effects:

The hydro-mechanical coupling experimental device with the CT real-time scanning provided by the present disclosure is provided with the support frame, the hydro-mechanical coupling mechanism and the jack; and the experimental box of the hydro-mechanical coupling mechanism and the movable plate of the support frame are made of carbon fiber materials that can be penetrated by X-rays. During experiment, the coal and rock sample is placed between the compression leg and the pressure box, the purified water is accessed into the experimental box to immerse the coal and rock sample, at this time the mechanical properties of the immersed coal and rock mass are simulated and reduced, the movable plate is jacked through the jack, and the movable plate drives the hydro-mechanical coupling mechanism to move up. When resisting to the top plate, the compression leg begins to generate pressure to the coal and rock sample, the pressure box can transmit real-time stress data to outside, so as to obtain the mechanical characteristics rules of the hydro-mechanical coupling coal and rock mass, and however the CT scanning room can perform the evolution rules for internal deformation of the CT scanning coal and rock sample, and the mesomechanics destructive characteristics inside the coal and rock mass are observed in real time.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are some rather than all of the embodiments of the present disclosure. The embodiments in the present disclosure and features in the embodiments can be combined with each other without conflict. Based on the embodiments of the present disclosure, all the other embodiments obtained by those of ordinary skill in the art on the premise of not contributing creative effort should belong to the protection scope of the present disclosure.

It is noted that if the embodiments of the present disclosure include directional indication, such as: upper, lower, left, right, front, rear, etc., the directional indication is merely used to explain the relative position relation, movement and the like of various components under a certain special posture as shown in the drawings; and if the special posture is changed, the directional indication will change accordingly.

In addition, if the embodiments of the present disclosure include the descriptions "first" and "second", the descriptions "first" and "second" are merely used for description, instead of being understood as indicating or implying relative importance or impliedly indicating the quantity of the showed technical features. Thus, the features defined with "first" and "second" can expressly or impliedly one or more features. In addition, the meaning of "and/or" in the text includes three parallel schemes, take "A and/or B" for example, including A scheme, or B scheme, or the scheme meeting A and B at the same time. In addition, "a plurality of" means two or above two. Thus, the technical solutions of various embodiments can be mutually combined, but must be achieved by those of ordinary skill in the art. When the combination of the technical solution has mutual contradiction or cannot be achieved, it should believe that such combination of the technical solution does not exist and does not fall in the protection range required by the present disclosure.

Referring to FIG. 1 to FIG. 6, a hydro-mechanical coupling experimental device with CT real-time scanning provided by the present disclosure, including a CT scanning room 1, further including a support frame 2, a hydro-mechanical coupling mechanism 3 and a jack 4 that are arranged in the CT scanning room 1.

Figure 1:
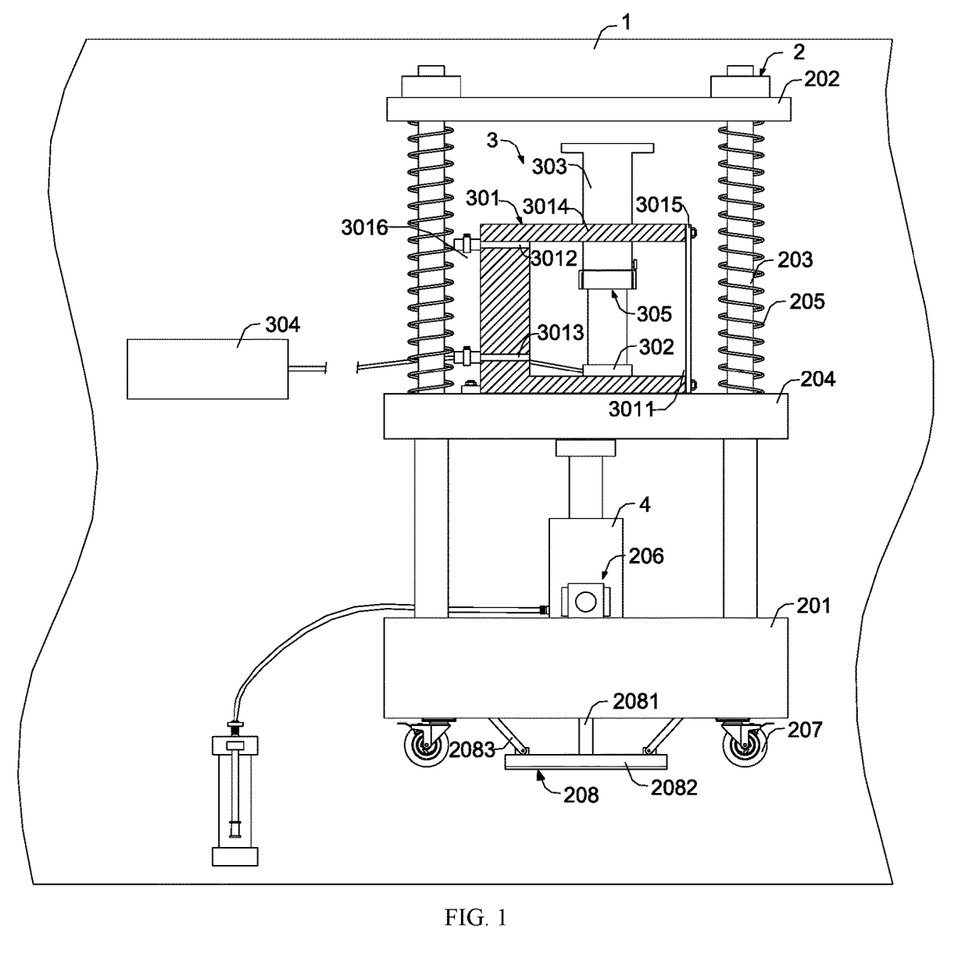
FIG. 1 is local section view of a front structure of a hydro-mechanical coupling experimental device with CT real-time scanning in the present disclosure.

The support frame 2 includes a base 201, a top plate 202, a plurality of columns 203 for arranging the top plate 202 and the base 201 at intervals, and a movable plate 204 that is arranged between the top plate 202 and the base 201 and can slide on the plurality of columns 203. The hydro-mechanical coupling mechanism 3 includes an experimental box 301, a pressure box 302 arranged inside the experimental box 301 and a compression leg 303 slidingly worn on a top of the experimental box 301; and the experimental box 301 is arranged on the movable plate 204, and the jack 4 is arranged on the base 201.

The hydro-mechanical coupling mechanism 3 further includes a regulating assembly 305, and the regulating assembly 305 includes an operation block 3051, a first threaded rod 3052 and two first limiting members 306.

Figure 2:
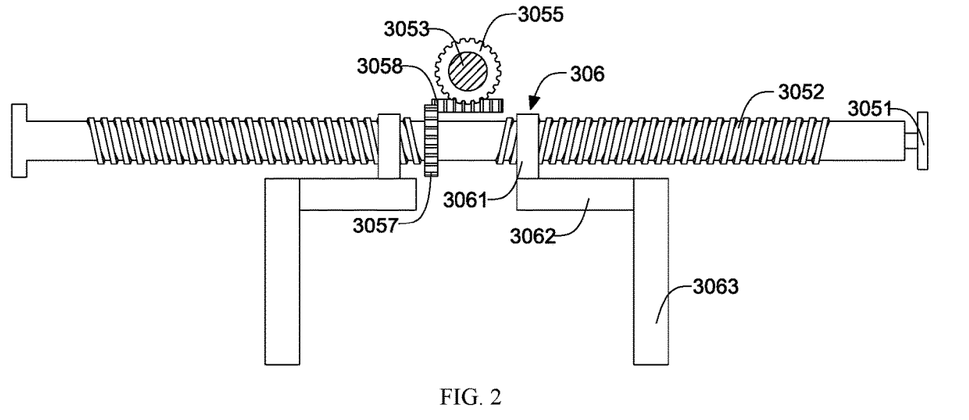
FIG. 2 is a side view of a local structure of a regulating assembly in the present disclosure.

One end, located in the experimental box 301, of the compression leg 303 is provided with a first installation groove 3031, screws at two sides of the first threaded rod 3052 are symmetrically arranged, two ends of the first threaded rod 3052 are rotationally arranged on groove walls of two sides of the first installation groove 3031 in respective, and one end of the first threaded rod 3052 passes through the first installation groove 3031 and the compression leg 303 to be connected to the operation block 3051; and the two first limiting members 306 are in threaded connection with the two sides of the first threaded rod 3052 in respective, and the two first limiting members 306 are slidingly connected to the groove wall of the first installation groove 3031 in respective.

The hydro-mechanical coupling experimental device with the CT real-time scanning provided by the present disclosure is provided with the support frame 2, the hydro-mechanical coupling mechanism 3 and the jack 4; and the experimental box 301 of the hydro-mechanical coupling mechanism 3 and the movable plate 204 of the support frame 2 are made of carbon fiber materials that can be penetrated by X-rays. During experiment, the coal and rock sample is placed between the compression leg 303 and the pressure box 302, the purified water is accessed into the experimental box 301 to immerse the coal and rock sample, at this time the mechanical properties of the immersed coal and rock mass are simulated and reduced, the movable plate 204 is jacked through the jack 4, and the movable plate 204 drives the hydro-mechanical coupling mechanism 3 to move up. When resisting to the top plate 202, the compression leg 303 begins to generate pressure to the coal and rock sample, the pressure box 302 can transmit the real-time stress data to outside, so as to obtain the mechanical characteristics rules of the hydro-mechanical coupling coal and rock mass, and however the CT scanning room 1 can perform the evolution rules for internal deformation of the CT scanning coal and rock sample, and the mesomechanics destructive characteristics inside the coal and rock mass are observed in real time.

Figure 4:
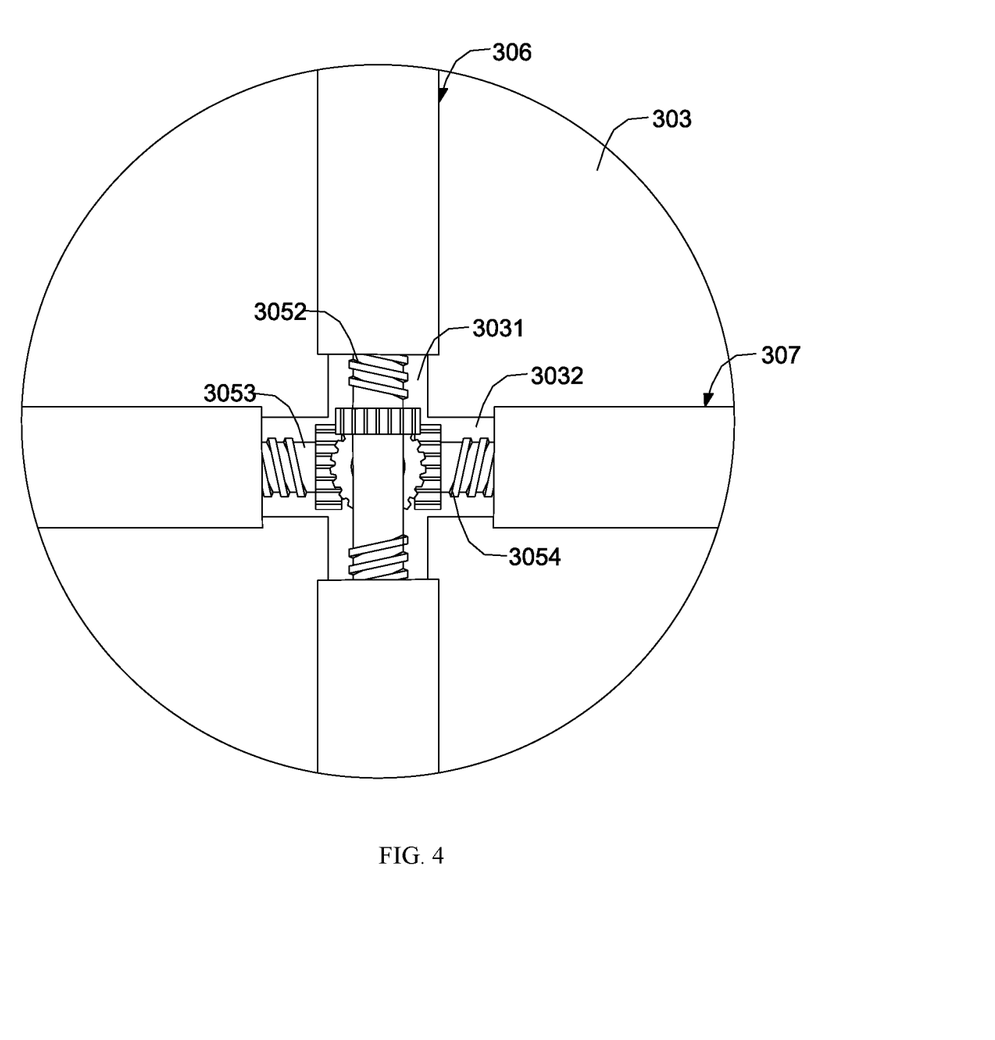
FIG. 4 is a bottom view of a local structure of a compression leg in the present disclosure.

In this present disclosure, the arranged first installation groove 3031 is strip, and the first installation groove 3031 is arranged at a central position of the compression leg 303, so that the two first limiting members 306 are symmetrically arranged in relative to the compression leg 303. Through this design, when the coal and rock sample is on the pressure box 302, a part of the coal and rock sample is located between the two first limiting members 306, which can limit the coal and rock sample inside the experimental box 301 in two directions, so that the coal and rock sample is located at a central position between the compression leg 303 and the pressure box 302, and then the coal and rock sample can be prevented from sliding when subjected to the pressure; and however the two first limiting members 306 can regulate a limiting distance along the rotation of the operation block 3051, so as to adapt to the coal and rock sample of different sizes.

In the present disclosure, the support frame 2 is provided with four columns 203, which are symmetrically arranged between the base 201 and the top plate 202, to help to strengthen the stability of the support frame 2. The jack 4 adopts a separating electric jack, an operation end is located outside the device of the present disclosure, a fixed output end is arranged on the base 201 to push the movable plate 204, thereby helping an experimenter to operate the jack 4.

In one embodiment, the experimental box 301 includes a housing 3014 with an operation port 3011, a water inlet 3013 and a water outlet 3012, a tempered transparent glass plate 3015 for sealing the housing 3014 and two valves 3016 for controlling the water inlet 3013 and the water outlet 3012 to be opened and closed. In this embodiment, the tempered transparent glass plate 3015 is fixed with the housing 3014 by tightening a pin and the operation port 3011 is sealed, so that the tempered transparent glass plate 3015 is convenient to disassemble and install and the coal and rock sample is convenient to be placed on the pressure box 302 through the operation port 3011, and at the same time, with great hardness, the tempered transparent glass plate 3015 is not easily crushed when being impacted, and the evolution rules of the surface morphology of the coal and rock sample are convenient to observe from outside. The arranged water inlet 3013 is located below the water inlet 3012, and the water outlet 3012 is arranged along a top wall inside the housing 3014. When injecting water in the sealed housing 3014, the valves 3016 of the water outlet 3012 and the water inlet 3013 are opened, purified water is accessed into the water inlet 3013, air inside the sealed housing 3014 is discharged through the water inlet 3012, so that the sealed housing 3014 is filled with the experimental purified water conveniently, and the arranged valves 3016 are configured to create a closed environment and to control water to flow in and out conveniently.

In one embodiment, the hydro-mechanical coupling mechanism 3 further includes a stress-strain data acquisition instrument 304; a trunking, through which a data wire of the pressure box 302 can pass through, is also arranged on the housing 3014; and a waterproof gasket is arranged on a groove wall of the trunking, and the stress-strain data acquisition instrument 304 is connected to the pressure box 302 through the data wire. Through this design, stress data obtained from the pressure box 302 can be collected in real time through the stress-strain data acquisition instrument 304 during an experiment process, and the waterproof gasket is configured to ensure the impermeability of the experimental box 301.

Figure 3:
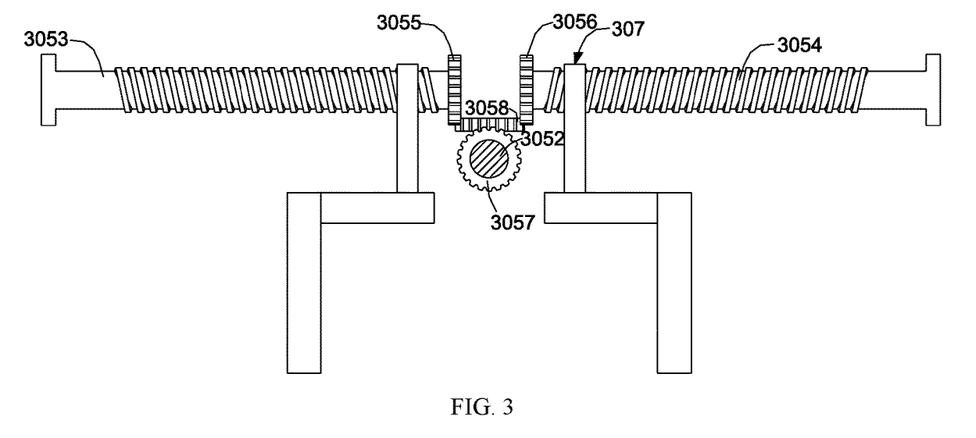
FIG. 3 is a side view of a local structure of a regulating assembly in the present disclosure.

In one embodiment, the regulating assembly 305 further includes a second threaded rod 3053, a third threaded rod 3054 and two second limiting members 307 that are symmetrically arranged.

One end, located in an experimental box 301, of a compression leg 303 is also provided with a second installation groove 3032 communicating with a first installation groove 3031, one end of the second threaded rod 3053 is rotationally connected to a groove wall of one side of the second installation groove 3032 while the other end is connected to a first gear 3055, and one end of the third threaded rod 3054 is rotationally connected to a groove wall of the other side of the second installation groove 3032 while the other end is connected to a second gear 3056; and the two second limiting members 307 are in threaded connection with the second threaded rod 3053 and the third threaded rod 3054 in respective, and the two second limiting members 307 are slidingly connected to the groove wall of the second installation groove 3032 in respective.

A third gear 3057 is arranged in a middle of a first threaded rod 3052, a fourth gear 3058 is rotationally arranged on a groove wall of the first installation groove 3031, the fourth gear 3058 meshes with the third gear 3057, and the first gear 3055 and the second gear 3056 mesh with two sides of the fourth gear 3058 in respective. In this embodiment, the arranged second installation groove 3032 is also strip, the second installation groove 3032 and the first installation groove 3031 are arranged in a crossed-shape, and a communicating position of the second installation groove 3023 and the first installation groove 3031 is located at the central position of the compression leg 303. Through this design, the coal and rock sample can be limited again in other two directions, so that the limiting effect is better, and when the first limiting members 306 are regulated, the second limiting members 307 can be regulated along the operation block 3051, so the regulation is convenient.

In one embodiment, the first limiting members 306 and the second limiting members 307 are of the same structure and all include a sliding block 3061, a connecting strip 3062 connected to the sliding block 3061, and a baffle 3063 vertically connected to the connecting strip 3062. In this embodiment, two sliding blocks 3061 of the two first limiting members 306 are in threaded connection with the two sides of the first threaded rod 3051 in respective and in sliding connection with the groove wall of the first installation groove 3031 in respective; two sliding blocks 3061 of the two second limiting members 307 are in threaded connection with the second thread rod 3053 in respective, in threaded connection with the third threaded rod 3054, and in sliding connection with the groove wall of the second installation groove 3032 in respective; and the four connecting strips 3062 and the baffle 3063 are symmetrically arranged on the compression leg 303, and the limiting effect can be implemented well through this design.

In one embodiment, a spring 205 is wound on each column 203, and the spring 205 is located between the movable plate 204 and the top plate 202; and two ends of the spring 205 are respectively connected to the movable plate 204 and the top plate 202. Through this design, a buffer zone is designed through the spring 205, so that the compression leg 303 is subjected to pressure after rising stably and resisting to the top plate 202 when the jack 4 is started.

Figure 5:
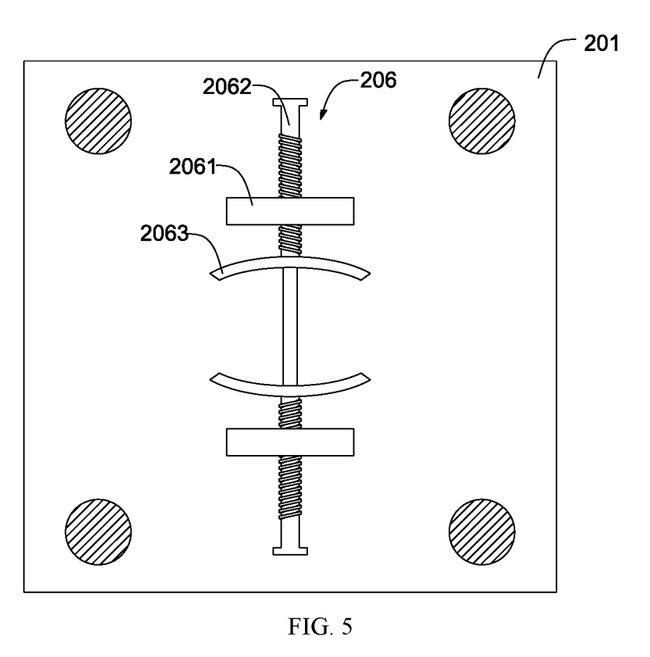
FIG. 5 is a schematic diagram of a structural position of a fixed assembly in the present disclosure.

In one embodiment, the support frame 2 further includes two fixed assemblies 206 that are symmetrically arranged, and each fixed assembly 206 includes a fixed plate 2061, a fourth threaded rod 2062 and a fixed block 2063.

The fixed plate 2061 is arranged on the base 201, the fourth threaded rod 2062 is in threaded connection with the fixed plate 2061, and the fixed block 2063 is rotationally connected to one end of the fourth threaded rod 2062 and slidingly connected to the base 201. In this embodiment, a cross section of the arranged fixed plate 2061 is circular, which is convenient to fit with an outer surface of the jack 4. In this design, the two fixed assemblies 206 can be regulated to clamp the jack 4 fixedly through the rotation of the fourth threaded rod 2062, so that the jack 4 is more convenient to disassemble and fix.

A use method for a hydro-mechanical coupling experimental device with CT real-time scanning, which is applied in a hydro-mechanical coupling experimental device with the CT real-time scanning, and the steps are as follows:

S1: preparing a standard coal and rock sample; and in this step, the prepared coal and rock sample is a cuboid structure, with a size of 50 mm long×50 mm wider 100 mm high;

S2: opening a tempered transparent glass plate 3015, placing the coal rock sample on a pressure box 302, and regulating a regulating assembly 305 so that the coal rock sample is adjusted and located at a central position of the pressure box 302 and a top of the coal rock sample is partially located between first limiting members 306 and second limiting members 307;

S3: fixing the tempered transparent glass plate 3015, sealing a housing 3014, opening valves 3016 of a water inlet 3013 and a water outlet 3012, accessing purified water with pressure into the sealed housing 3014 through the water inlet 3013 until a whole experimental box 301 is full of the purified water, and closing the valves 3016 of the water inlet 3013 and the water outlet 3012; in this step, the purified water with the pressure is accessed into the sealed housing 3014 from the water inlet 3013 through a self-priming pump and a booster pump, and the accessed purified water includes 5% of emulsified liquid, which can prevent some components inside the experimental box 301 from being rusted due to being located in the purified water, a pressure valve of the purified water can be adjusted through the booster pump in different experiments, so that experimental data of the coal and rock sample under different pressure values can be obtained conveniently.

S4: standing the coal and rock sample in the purified water for a period of time, where the time range is 24-48 hours, and the coal and rock sample that is always in a hydraulic pressure environment is simulated; and S5: after standing, opening a jack 4 to push a movable plate 204, opening CT scanning and receiving equipment of a CT scanning room 1 and opening a stress-strain data acquisition instrument 304 for data acquisition, and recording a strength, a deformation, a surface morphology and evolution rules of mesomechanics destructive characteristics of the sample in real time under in-situ loading conditions of hydro-mechanical coupling.

Figure 6:
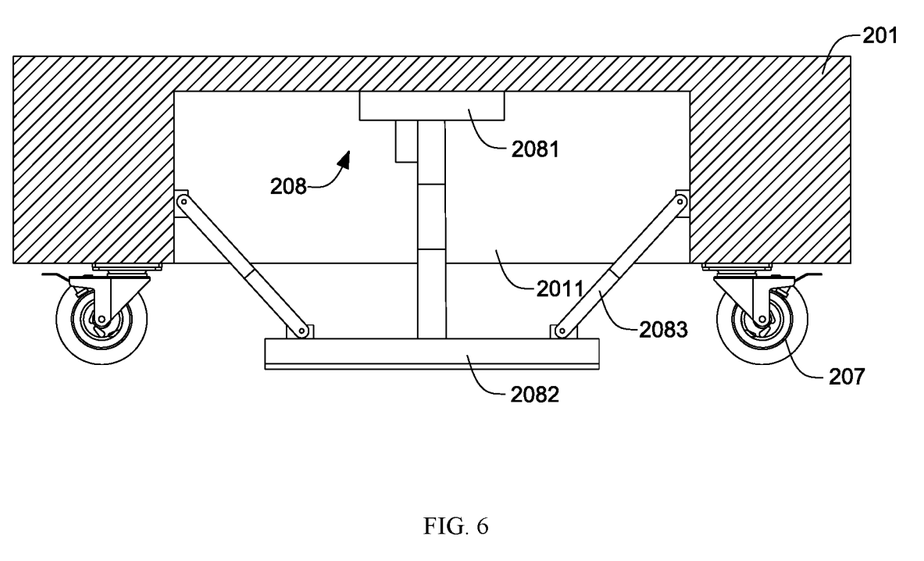
FIG. 6 is a section view of a base structure in the present disclosure.

In one embodiment, the support frame 2 further includes a plurality of pulleys 207 and a locating assembly 208.

The locating assembly 208 includes an electric push rod 2081, a locating plate 2082 connected to an output end of the electric push rod 2081, and two expansion rods 2083 of which one ends are respectively hinged with two sides of the locating plate 2082; and a groove 2011 is formed in the base 201, a fixed end of the electric push rod 2081 is arranged in the groove 2011, the other ends of the two expansion rods 2083 are respectively hinged with groove walls of the two sides of the groove 2011, and the plurality of pulleys 207 are arranged at a bottom of the base 201 at intervals. In this embodiment, four pulleys 207 are arranged; and the pulleys 207 are arranged at the two sides of the bottom of the base 201 in pairs. In this design, the convenient carrying of the device can be implemented through the plurality of pulleys 207, and at the same time the arranged locating assembly 208 can be pushed through the electric push rod 2081 so as to take back the locating plate 2082 and implement whether the locating plate 2082 contacts with the ground or not, that is, when the whole device is fixed, the locating plate 2082 resists to the ground, so as to prevent the pulleys 207 from sliding freely, and the locating plate 2082 is taken back when moving the device.

It should be understood that the examples and implementation modes of the present disclosure are merely for description, not intended to limit the present disclosure. Those skilled in the art can make various modifications or changes, and any modifications, equivalent replacements, improvements and the like made within the spirit and principle of the present disclosure shall fall within the protection scope of the present disclosure.

What is claimed is:

1. A hydro-mechanical coupling experimental device with computed tomography (CT) real-time scanning, comprising a CT scanning room wherein the device further comprises a support frame, a hydro-mechanical coupling mechanism and a jack that are arranged in the CT scanning room;

the support frame comprises a base, a top plate, a plurality of columns for arranging the top plate and the base at intervals, and a movable plate that is arranged between the top plate and the base and capable of sliding on the plurality of columns; the hydro-mechanical coupling mechanism comprises an experimental box, a pressure box arranged inside the experimental box and a compression leg slidingly worn on a top of the experimental box; and the experimental box is arranged on the movable plate, and the jack is arranged on the base;

the hydro-mechanical coupling mechanism further comprises a regulating assembly, and the regulating assembly comprises an operation block, a first threaded rod and two first limiting members; and one end, located in the experimental box, of the compression leg is provided with a first installation groove, screws at two sides of the first threaded rod are symmetrically arranged, two ends of the first threaded rod are rotationally arranged on groove walls of two sides of the first installation groove in respective, and one end of the first threaded rod passes through the first installation groove and the compression leg to be connected to the operation block; and the two first limiting members are in threaded connection with the two sides of the first threaded rod in respective, and the two first limiting members are slidingly connected to the groove wall of the first installation groove in respective.

2. The hydro-mechanical coupling experimental device with the CT real-time scanning according to claim 1, wherein the experimental box comprises a housing with an operation port, a water inlet and a water outlet, a tempered transparent glass plate for sealing the housing and two valves for controlling the water inlet and the water outlet to be opened and closed.

3. The hydro-mechanical coupling experimental device with the CT real-time scanning according to claim 2, wherein the hydro-mechanical coupling mechanism further comprises a stress-strain data acquisition instrument; a trunking, through which a data wire of a pressure box passes through, is also arranged on the housing; and a waterproof gasket is arranged on a groove wall of the trunking, and the stress-strain data acquisition instrument is connected to the pressure box through the data wire.

4. The hydro-mechanical coupling experimental device with the CT real-time scanning according to claim 3, wherein the regulating assembly further comprises a second threaded rod, a third threaded rod and two second limiting members that are symmetrically arranged;

one end, located in an experimental box, of a compression leg is also provided with a second installation groove communicating with the first installation groove, one end of the second threaded rod is rotationally connected to a groove wall of one side of the second installation groove while the other end is connected to a first gear, and one end of the third threaded rod is rotationally connected to a groove wall of the other side of the second installation groove while the other end is connected to a second gear; and the two second limiting members are in threaded connection with the second threaded rod and the third threaded rod in respective, and the two second limiting members are slidingly connected to the groove wall of the second installation groove in respective; and a third gear is arranged in a middle of the first threaded rod, a fourth gear is rotationally arranged on a groove wall of the first installation groove, the fourth gear meshes with the third gear, and the first gear and the second gear mesh with two sides of the fourth gear in respective.

5. The hydro-mechanical coupling experimental device with the CT real-time scanning according to claim 4, wherein first limiting members and the second limiting members are of the same structure and all comprise a sliding block, a connecting strip connected to the sliding block, and a baffle vertically connected to the connecting strip.

6. The hydro-mechanical coupling experimental device with the CT real-time scanning according to claim 1, wherein a spring is wound on each column, and the spring is located between the movable plate and the top plate; and two ends of the spring are respectively connected to the movable plate and the top plate.

7. The hydro-mechanical coupling experimental device with the CT real-time scanning according to claim 1, wherein the support frame further comprises two fixed assemblies that are symmetrically arranged, and each fixed assembly comprises a fixed plate, a fourth threaded rod and a fixed block; and the fixed plate is arranged on the base, the fourth threaded rod is in threaded connection with the fixed plate, and the fixed block is rotationally connected to one end of the fourth threaded rod and slidingly connected to the base.

8. A use method for a hydro-mechanical coupling experimental device with CT real-time scanning, which is applied in a hydro-mechanical coupling experimental device with CT real-time scanning according to claim 4, and the steps are as follows:

S1: preparing a standard coal and rock sample;

S2: opening a tempered transparent glass plate, placing the coal and rock sample on a pressure box, and regulating a regulating assembly so that the coal and rock sample is adjusted and located at a central position of the pressure box and a top of the coal and rock sample is partially located between first limiting members and second limiting members;

S3: fixing the tempered transparent glass plate, sealing a housing, opening valves of a water inlet and a water outlet, accessing purified water with pressure into the sealed housing through the water inlet until a whole experimental box is full of the purified water, and closing the valves of the water inlet and the water outlet;

S4: standing the coal and rock sample in the purified water for a period of time, wherein the time range is 24-48 hours; and S5: after standing, opening a jack to push a movable plate, opening CT scanning and receiving equipment of a CT scanning room and opening a stress-strain data acquisition instrument for data acquisition, and recording a strength, a deformation, a surface morphology and evolution rules of mesomechanics destructive characteristics of the sample in real time under in-situ loading conditions of hydro-mechanical coupling.

* * * * *